US008186210B2

(12) United States Patent
Hangen

(10) Patent No.: US 8,186,210 B2
(45) Date of Patent: May 29, 2012

(54) SURFACE EVALUATION EMPLOYING ORTHOGONAL FORCE MEASUREMENT

(75) Inventor: Ude Dirk Hangen, Aachen (DE)

(73) Assignee: Hysitron Incorporated, Minneapolis, MN (US)

(*) Notice: Subject to any disclaimer, the term of this patent is extended or adjusted under 35 U.S.C. 154(b) by 462 days.

(21) Appl. No.: 12/471,036

(22) Filed: May 22, 2009

(65) Prior Publication Data
US 2009/0320575 A1 Dec. 31, 2009

Related U.S. Application Data

(60) Provisional application No. 61/055,750, filed on May 23, 2008.

(51) Int. Cl.
*G01N 17/00* (2006.01)
(52) U.S. Cl. ..................................................... 73/150 R
(58) Field of Classification Search .................. None
See application file for complete search history.

(56) References Cited

U.S. PATENT DOCUMENTS

| 5,661,235 | A | 8/1997 | Bonin |
| 6,520,004 | B1 | 2/2003 | Lin |
| 6,640,459 | B1 | 11/2003 | Lucas et al. |
| 2004/0011119 | A1 | 1/2004 | Jardret et al. |
| 2006/0137469 | A1 | 6/2006 | Yang et al. |
| 2006/0191327 | A1 | 8/2006 | Yang et al. |

FOREIGN PATENT DOCUMENTS

WO 0218905 3/2002

OTHER PUBLICATIONS

PCT Search Report, PCT/US2009/045191, filed Mar. 26, 2009, Hysitron Incorporated.

*Primary Examiner* — Robert R Raevis
(74) *Attorney, Agent, or Firm* — Dicke, Billig & Czaja PLLC

(57) ABSTRACT

A method for evaluating a performance of a substrate surface including applying a normal force with a probe to a surface of a substrate, the normal force being substantially perpendicular to the surface, and moving the probe across the surface to generate a force against and to scratch the surface, the force being substantially parallel to the surface and comprising a coaxial force along the scratch and an orthogonal force perpendicular to the scratch. The method further includes measuring a magnitude of the orthogonal force as the probe moves across the coating, and determining a fracture point of the surface by the probe based on changes in the magnitude of the orthogonal force.

20 Claims, 8 Drawing Sheets

SURFACE EVALUATION EMPLOYING ORTHOGONAL FORCE MEASUREMENT

CROSS-REFERENCE TO RELATED APPLICATIONS

This Utility Patent Application claims benefit of U.S. Provisional Application 61/055,750, filed May 23, 2008, and which is incorporated herein by reference.

BACKGROUND OF THE INVENTION

Devices are commonly coated with thin films and other coatings in order to enhance their performance and functionality. Such coatings can be broadly characterized as being either hard coatings or soft coatings. Hard coatings, such as ceramic and diamond-like carbon, for example, are often applied to cutting tools to enhance their cutting ability and durability. Soft coatings, such as polymer-based materials, for example, are often applied to medical devices to improve their bio-compatibility.

Scratch tests are often performed on such coatings to study the mechanical behavior of the surface in terms of wear resistance or resistance against scratching. When performing such scratch tests, a scratch or indenter probe is pressed against the surface of the device with a normal force (i.e. perpendicular to the surface) and moved across the surface of the device, thereby creating a so-called lateral or coaxial force (i.e. parallel to the surface in the direction of probe movement) to scratch the coating. In some instances, the normal force is a constant force, while in other instances, the normal force is "ramped up" (e.g. in a linear fashion) as the indenter probe is moved across the surface.

When ramping the normal force while scratching the surface, the coating along the scratch track typically displays a fully elastic deformation regime, followed by a plastic deformation regime, and finally fracture. The transition from plastic deformation to fracture (the point of fracture) indicates a critical normal force which is used to rate the performance of the surface. In order to identify the point of fracture, conventional techniques often study the surface friction (i.e. ratio of coaxial force to normal force), or study the coaxial force in combination with visual observations of the scratch track.

However, due to a changing coefficient of friction, it is often difficult to determine the fracture point using friction analysis. Also, fractures in the coating are often too small to accurately identify, even with a microscope, while "scattering" or changes in the coaxial force are often inconsistent. Other techniques sometimes used to identify the fracture probe include study of normal displacement of the indenter probe (i.e. vertically relative to the surface) and acoustical transmissions. In any case, however, each of these approaches often provides inconsistent results and, as such, do not always successfully provide a reproducible pattern of fracture starts between multiple samples of a same device.

SUMMARY OF THE INVENTION

One embodiment provides a method for evaluating a performance of a substrate surface. The method includes applying a normal force with a probe to a surface of a substrate, the normal force being substantially perpendicular to the surface, and moving the probe across the surface to generate a force against and to scratch the surface, the force being substantially parallel to the surface and comprising a coaxial force along the scratch and an orthogonal force perpendicular to the scratch. The method further includes measuring a magnitude of the orthogonal force as the probe moves across the surface, and determining a fracture point of the surface by the probe based on changes in the magnitude of the orthogonal force.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be used and structural or logical changes may be made without departing from the scope of the present invention. The following detailed description, therefore, is not to be taken in a limiting sense, and the scope of the present invention is defined by the appended claims.

According to embodiments described herein, a system and method are provided for evaluating a performance of a thin film or coating applied to a substrate, such as the surface of a medical device, for example. According to one embodiment, the system and method includes applying normal and coaxial forces to the coating with a probe so as to scratch the coating, and determining a fracture point of the coating based on changes in magnitude of a resulting orthogonal force on the probe. According to one embodiment, a performance rating of the coating is based on a magnitude of the normal force at the coating fracture point.

Figure 1:
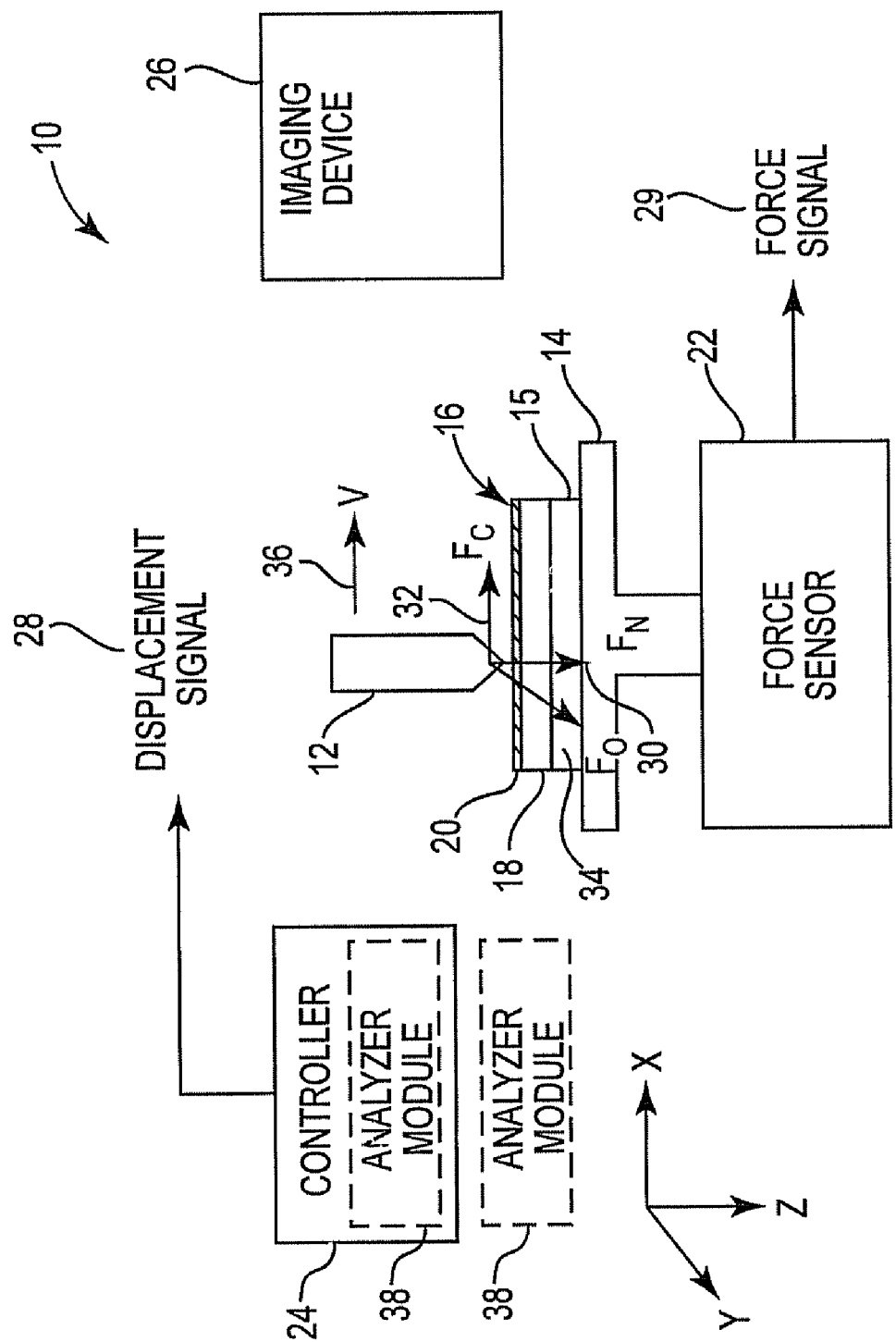
FIG. 1 is a block diagram illustrating one embodiment of a measuring apparatus according to the present invention.

FIG. 1 illustrates an example of a measuring apparatus 10 for conducting scratch tests of a thin film or coating applied to a substrate, according to one embodiment of the present disclosure. According to one embodiment, measuring apparatus 10 includes a scratch probe 12, and a platform 14 configured to hold a device, or at least a sample 16 of a device comprising a substrate or a material 18 having a surface 20 which is to be scratch tested. According to one embodiment, as illustrated by FIG. 1, surface 20 comprises a thin-film or coating 20 which has been joined to substrate or material 18. In one embodiment, as illustrated, measuring apparatus 10 further includes a holding device 15 which is selectively coupled to platform 14 and configured to engage and secure sample 16 so that it is not damaged prior to testing.

Measuring device 10 further includes a force sensor 22, a controller 24, and an imaging device 26. Controller 24 is configured to control movement of scratch probe 12 in the x, y and z dimensions relative to platform 14, and to provide a displacement signal 28 representative of displacement of scratch probe 12 in said dimensions from an initial reference point. Force sensor 22 is configured to measure a normal force ($F_N$) 30, a coaxial force ($F_C$) 32, and an orthogonal force ($F_O$) 34 between scratch probe 12 and device 16 as scratch probe 12 moves laterally across device 16 at a scratch velocity (V) 36, with coaxial force ($F_C$) 32 being along the axis of movement and orthogonal force ($F_O$) 34 being perpendicular to the axis of movement. According to one embodiment, force sensor 22 provides a force signal 29 representative of the measured normal, coaxial, and orthogonal forces 30, 32, and 34.

Measuring apparatus 10 further includes an imaging device 26 or other instrument/device capable of recording or determining the profile or contour of a test region, such as an optical microscope, a profilometer, a scanning probe microscope (SPM) or an atomic force microscope (AFM), and is configured to provide images of coating 20 and substrate 18 of sample 16. One example of an optical viewing device suitable to be configured for use as imaging device 26 is commercially available under the trade name Ziess Axio Imager Microscope from Carl Zeiss Microimaging, Incorporated of Thornwood, N.Y., USA.

Examples of systems similar to measuring apparatus 10 and suitable to be configured for use with this invention are described by U.S. Pat. Nos. 5,553,486 and 5,869,751, both of which are assigned to the same assignee as the present invention and are incorporated by reference herein. Test systems suitable to be configured for use with this present disclosure are commercially available from Hysitron Incorporated of Minneapolis, Minn., USA. For example, a Hysitron TriboIndenter system with a Hysitron 3D OmniProbe head attached is a suitable test system.

According to one embodiment of the present invention, measuring apparatus 10 is configured to perform an adhesion test, similar in nature to a "scratch" test, to measure the interfacial toughness, or work of adhesion, between coating 20 and substrate 18 to which it is joined. In one embodiment, controller 24 initially positions scratch probe 12 proximate to or in contact with coating 20 at a desired location on device 16. For example, in one instance, as illustrated by FIG. 2 below, it may be desirable to position scratch probe 12 away from edge locations of substrate 18, while in other instances, it may be desirable to position scratch probe 12 proximate to edges of substrate 18.

Figure 2:
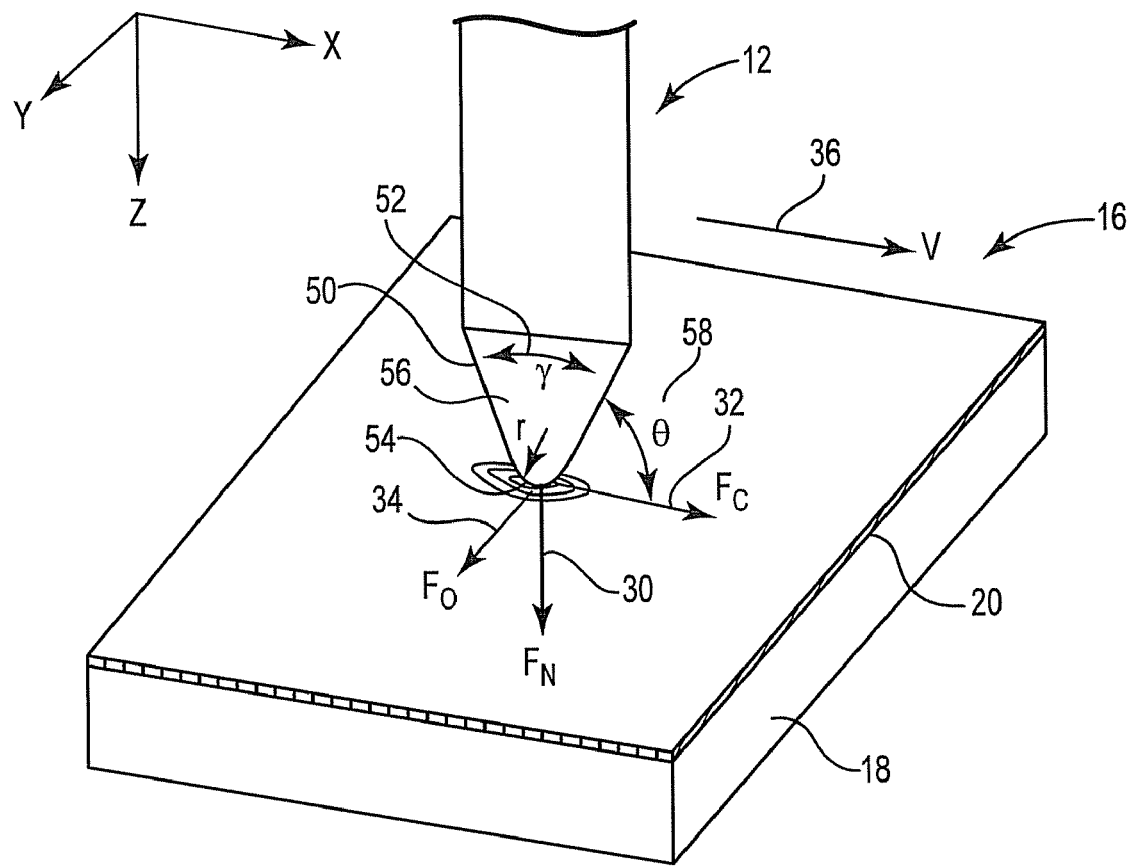
FIG. 2 is a perspective view of one embodiment of a scratch probe engaging a coating on a device.

FIG. 2 is a perspective view illustrating generally portions of one embodiment of scratch probe 12 in contact with a device 16. In one embodiment, as illustrated, scratch probe 12 comprises a cono-spherical probe with a conically-shaped portion 50 having an angle (γ) 52 which transitions to a spherical tip 54 for scratching coating 20 of device 16. However, scratch probe 12 can be of any axis-symmetric configuration, including conical or spherical, for example.

According to one embodiment, when scratch testing a coating of a sample, such as coating 20 of device 16, after initial positioning of scratch probe 12, controller 24 moves scratch probe 12 in the z-direction (downward toward platform 14 in FIG. 1) to apply normal force ($F_N$) 30 to device 16 with scratch probe 12. In one embodiment, concurrent with applying normal force 30, scratch probe 12 and platform 14 are moved laterally relative to one another (i.e. in the x-direction) at scratch velocity 36 so as to cause scratch probe 12 to apply coaxial force ($F_C$) 32 to device 16. In one embodiment, controller 24 causes scratch probe 12 to move laterally across device 16 by controlling lateral movement of scratch probe 12 while platform 14 remains laterally stationary. According to one alternative embodiment, controller 24 causes scratch probe 12 to move laterally across device 16 by controlling lateral movement of platform 14 while scratch probe 12 remains laterally stationary.

As scratch probe 12 moves laterally across device 16, force sensor 22 measures normal, coaxial, and orthogonal forces 30, 32, and 34 between scratch probe 12 and device 16 and provides force signal 29 indicative of the measured values of normal, coaxial, and orthogonal forces 30, 32, and 34. Concurrently, controller 24 provides displacement signal 28 indicative of the normal (z-direction) and lateral displacement (x-direction) of scratch probe 12 relative to device 16. In one embodiment, controller 24 controls scratch probe 12 so as to apply normal force $F_N$ 30 with a constant force or load to device 16. The magnitude of the constant normal load applied may depend upon the particular type of device being tested and upon various factors associated with coating 20.

It is noted that force sensor 22 employs three sensors, one to measure force in the x-direction, one to measure force in the y-direction, and one to measure force in the z-direction. As described above by the example of FIGS. 1 and 2, the probe is moved laterally across device such that the scratch and coaxial force $F_C$ 32 are along the x-axis. However, the scratch is not required to be made along one of the axes, and can be made in any direction on the surface of device 16. In an instance where the scratch direction is non-parallel to either the x- or the y-directions, force sensor 22 can calculate the coaxial and orthogonal forces $F_C$ and $F_O$ 32 and 34 from the sensed forces along the x- and y-axes based on a known scratch angle.

In one embodiment, controller 24 ramps normal force $F_N$ 30 from an unload condition (i.e. no load) to the desired constant load and maintains normal force $F_N$ 30 substantially at the desired constant load for a duration of a scratch operation. At the conclusion of the scratch operation, controller 24 returns normal force $F_N$ 30 from the desired constant load to an unload condition in an unload time. In one embodiment, the load and unload times each comprise approximately 0.1 seconds.

Figure 3A:
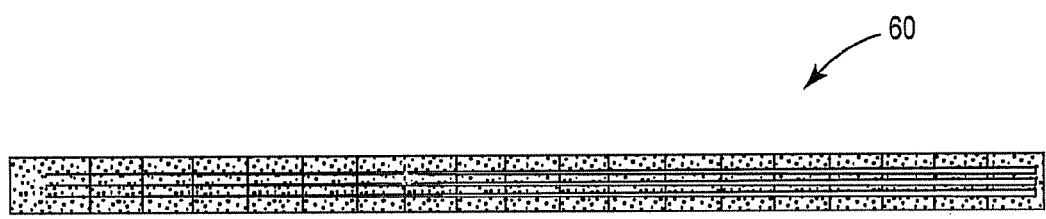
FIG. 3A is an image of a test sample after being scratched.
Figure 3B:
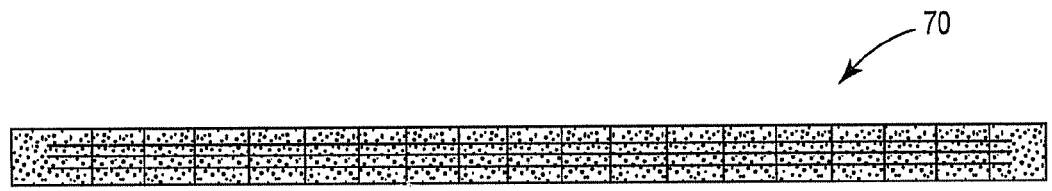
FIG. 3B is an image of a test sample after being scratched.

FIGS. 3A-6B below illustrate and describe the operation of measuring apparatus 10 to identify fracture points of surface coatings using the results of scratch tests performed on two test samples employing monitoring of orthogonal force $F_O$ 34 according to embodiments of the present disclosure. FIG. 3A is an image 60 of a first test sample, Sample A, which includes a soft lacquer coating on a metallic substrate. FIG. 3B is an image 70 of a second test sample, Sample B, which includes hard lacquer coating on a metallic substrate. As illustrated, three scratches, or scratch tracks, 10 mm in length were made from left-to-right in both Sample A and Sample B using scratch probe 12. For each sample, scratch probe 12 had a tip radius 56 of 5 μm and normal load or force $F_N$ 30 was ramped from 0 to 300 mN with a scratch velocity, V, 36 of 30 mm/min.

Figure 4A:
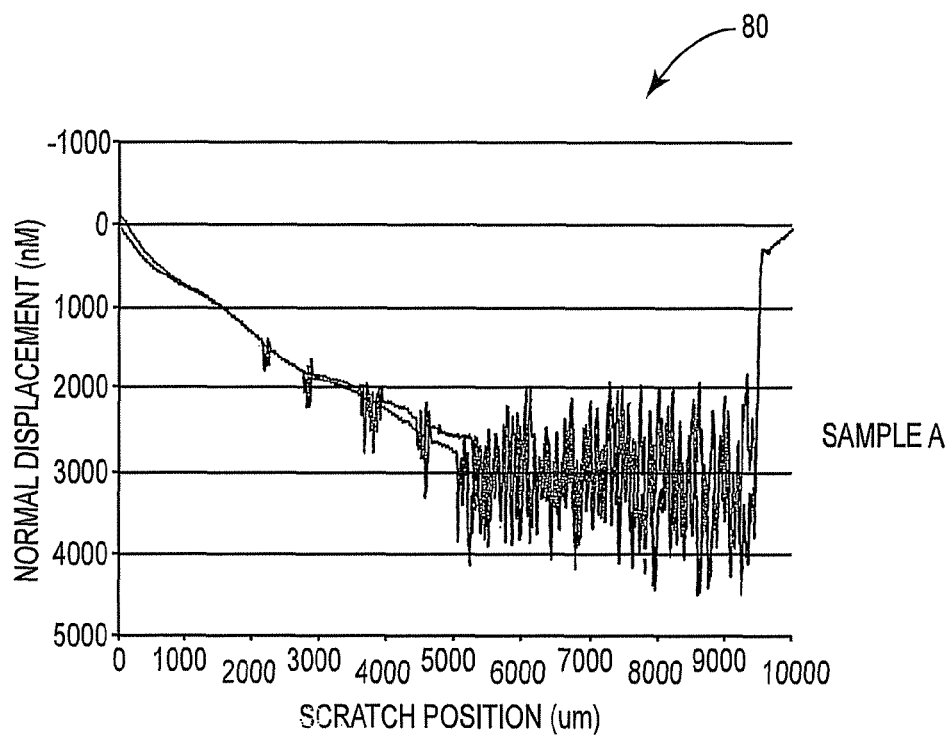
FIG. 4A is a graph of normal displacement of a scratch probe versus lateral position relative to a test sample.
Figure 4B:
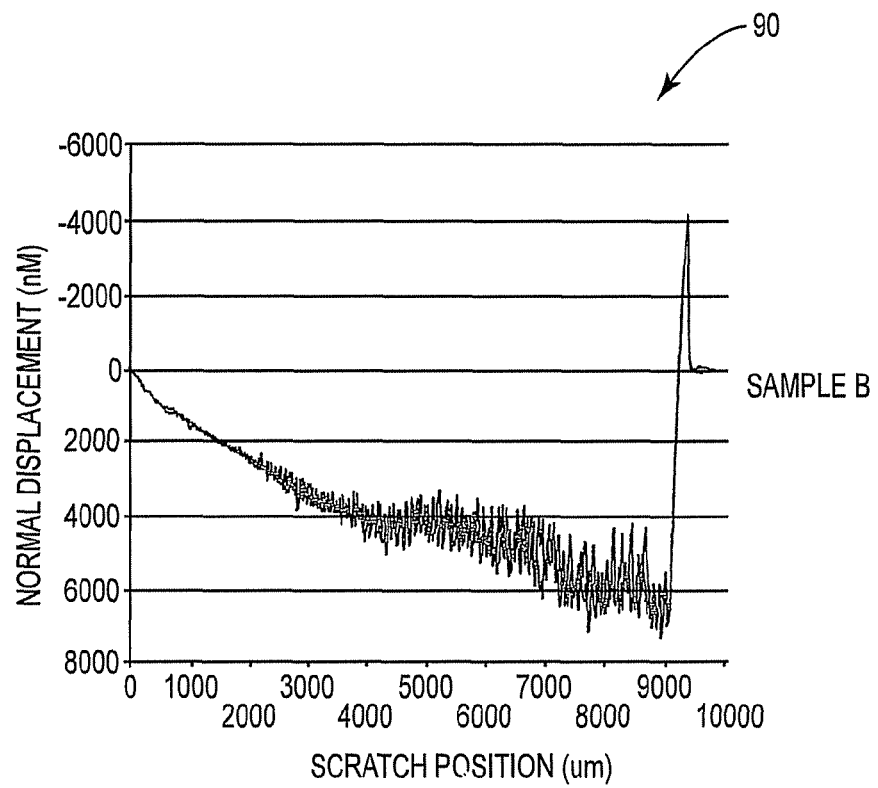
FIG. 4B is a graph of normal displacement of a scratch probe versus lateral position relative to a test sample.

FIGS. 4A and 4B are graphs 70 and 80 respectively illustrating the normal displacement (z-dimension) versus the lateral displacement (x-dimension) of scratch probe 12 as scratch probe 12 is moved laterally across Samples A and B. Graphs 70 and 80 are sometimes referred to as scratch profiles. It is noted that the normal displacement of scratch probe 12 for each of the three scratch tracks of the corresponding test sample is illustrated in each of the scratch profiles 70 and 80. It is also noted that the oscillations in scratch profiles 70 and 80 are due to cracking of the coating on Samples A and B.

Figure 5A:
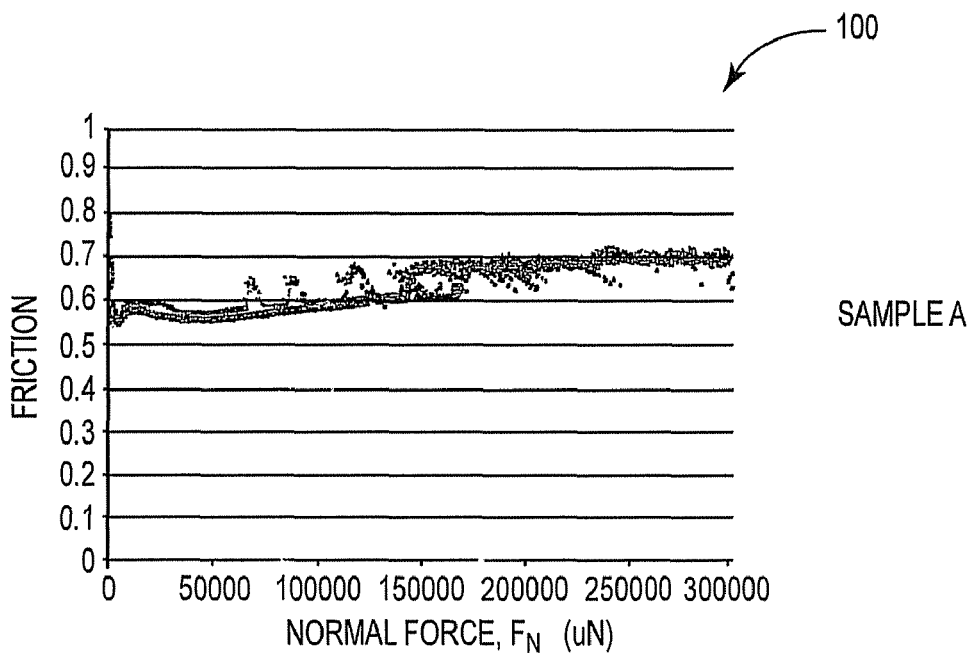
FIG. 5A is a graph of friction versus normal force for a test sample.
Figure 5B:
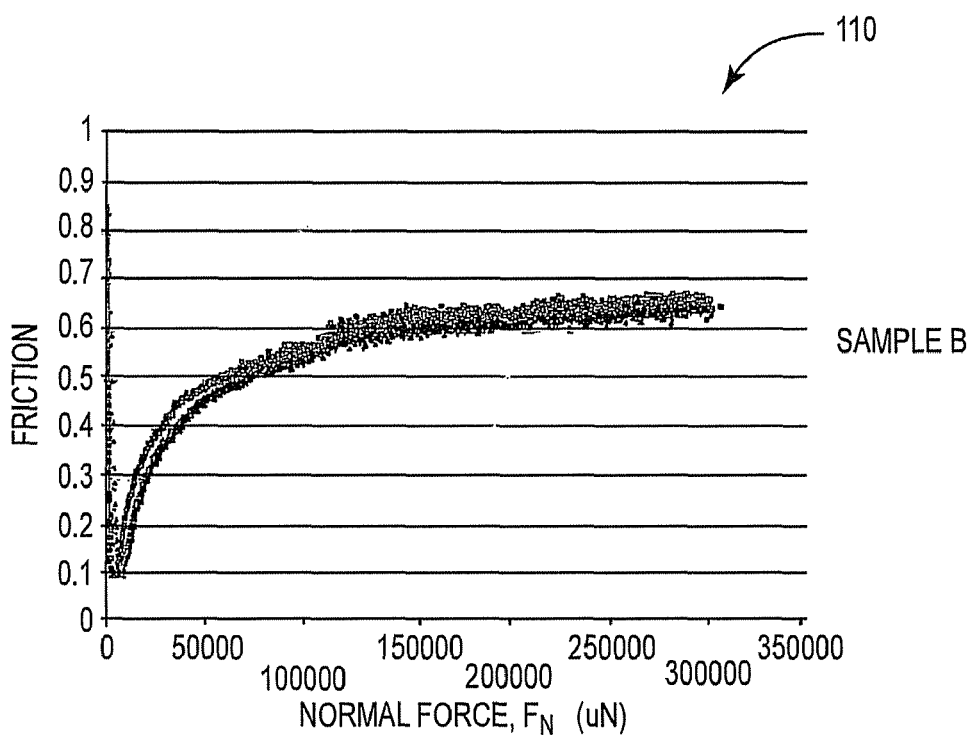
FIG. 5B is a graph of friction versus normal force for a test sample.

FIGS. 5A and 5B are graphs 100 and 110 respectively illustrating the friction between scratch probe 12 and Samples A and B versus the normal force $F_N$ 30, wherein the friction is defined as the ratio of coaxial force $F_C$ 32 to normal force $F_N$ 30. Again, it is noted that the friction of scratch probe 12 for each of the three scratch tracks of the corresponding test sample is illustrated in graphs 100 and 110.

According to conventional techniques, by observing the point at which significant scatter begins to appear in both the normal displacement illustrated by scratch profile 80 and the friction of graph 100, the critical or fracture point of the coating can be identified at approximately 130 mN for Sample A (i.e. soft lacquer coating). However, due to an increase in the coefficient of friction between scratch probe 12 and the coating of Sample B, it is difficult to identify a fracture point of the coating of Sample B based on identifying the onset of significant scatter in scratch profile 90 and friction plot 110.

Figure 6A:
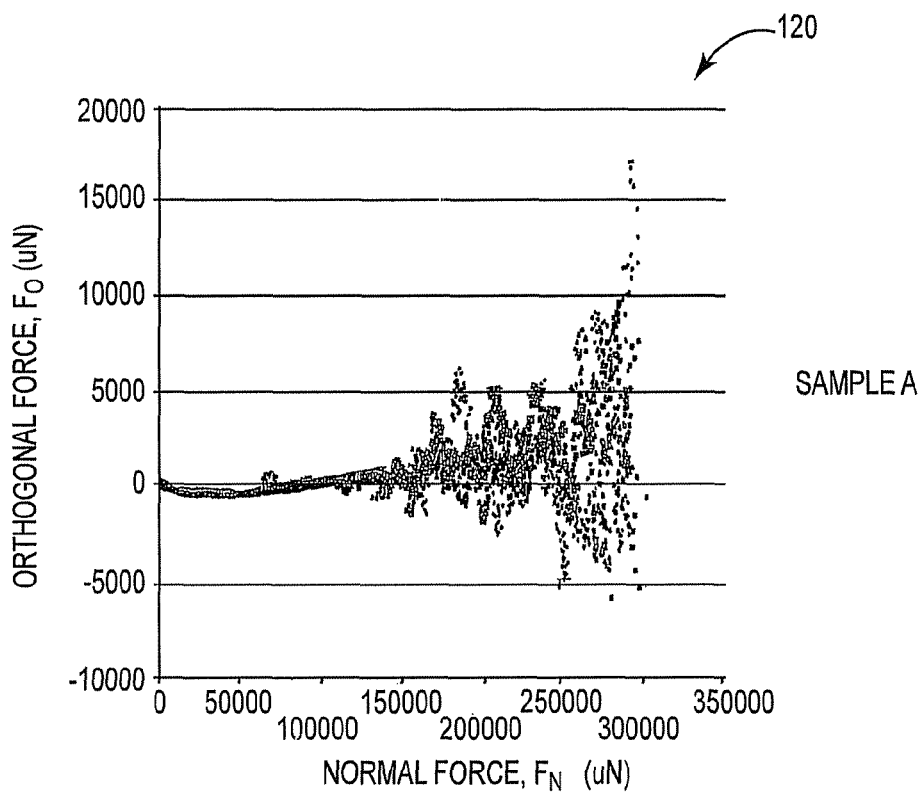
FIG. 6A is a graph of orthogonal force versus normal force for a test sample.
Figure 6B:
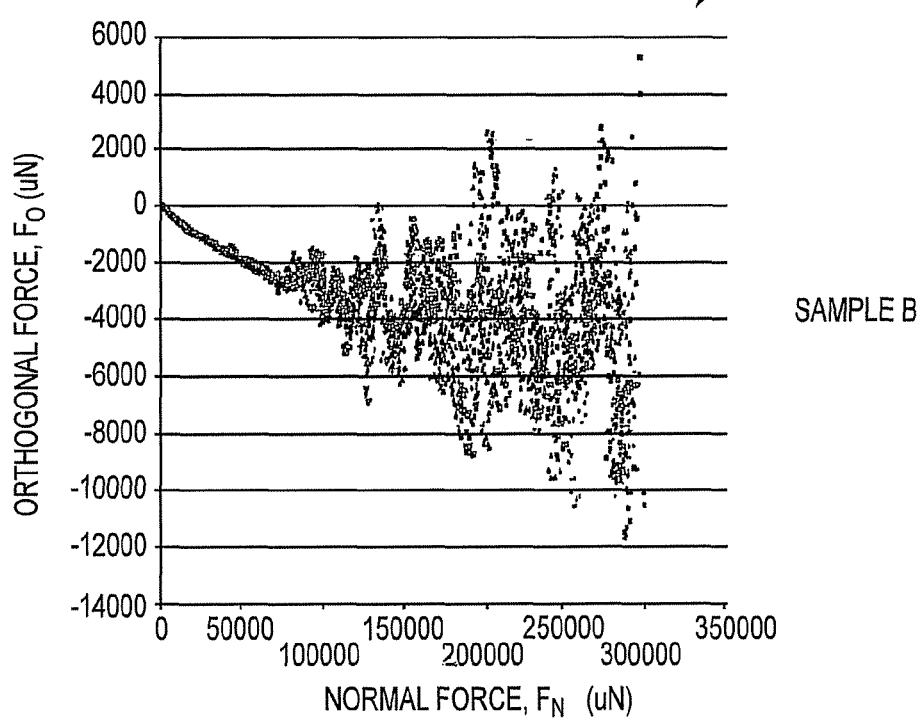
FIG. 6B is a graph of orthogonal force versus normal force for a test sample.

FIGS. 6A and 6B are graphs 120 and 130 respectively illustrating the orthogonal force $F_O$ 34 (y-dimension) versus the normal force $F_N$ 30 (z-dimension) as scratch probe 12 is moved laterally across Samples A and B, in accordance with the present disclosure. Again, it is noted that the orthogonal force $F_O$ 34 on scratch probe 12 for each of the three scratch tracks of the corresponding test sample is illustrated in each of the graphs 120 and 130. It is also noted that the oscillations in the magnitude of orthogonal force $F_O$ 34 are due to cracking of the coating on Samples A and B.

With reference to graphs 120 and 130, due to the clearly identifiable onset of an increase in scatter in the measurements of the orthogonal force $F_O$ 34, the critical or fracture point can be identified at approximately 130 mN of normal force $F_N$ 30 for the coating of Sample A, and at approximately 80 mN of normal force $F_N$ 30 for the coating of Sample B. As such, while conventional techniques were able to identify only the facture point of Sample A, the surface test method employing monitoring of orthogonal force $F_O$ 34 according to the present disclosure is able to clearly identify the critical or fracture point of the device coating in both Sample A and Sample B.

In summary, monitoring of orthogonal force $F_O$ 34 for fracture detection has several advantages over conventional approaches. First, as illustrated above by the testing of Samples A and B, unlike friction or normal displacement monitoring, the measurements of orthogonal force $F_O$ 34 were consistent and reproducible for each of the scratches of each sample. As such, orthogonal force sensing provides accurate and dependable fracture detection.

Second, because the cracking of the coating is almost never fully symmetrical, small cracks in the coating which are indicative of the critical or fracture point of the coating are not always detectable via microscopic observation are detectable by monitoring of the orthogonal force $F_O$ 34. The resolution limit of microscopes in approximately 1 µm which, in some instances, makes it impossible to see the microscopic cracks which are indicative of the fracture point the coating.

Third, the measurement of orthogonal force $F_O$ 34 is based on mechanical movement of the scratch probe and, thus, provides accurate and reproducible fracture detection most, if not all, type of coatings. For example, while monitoring of orthogonal force $F_O$ 34 provides accurate fracture detection for softer coating materials, such as lacquer, for example, acoustic signals associated with such materials are heavily damped and not always able to provide accurate or consistent fracture detection.

Fourth, slower fracture events, such as debonding or tearing of a material or material interface with a substrate, often are difficult to detect using optical, acoustic, or coaxial force monitoring since such events often produce asymmetrical forces which may only be detectable using orthogonal or multi-directional force sensing.

Finally, fracture detection employing detection of orthogonal force $F_O$ 34 may be performed on any sample with normal force $F_N$ 30 being constant or changed while scratching (e.g. ramped). The measurements of orthogonal force $F_O$ 34 are not limited to the geometry of scratch probe 12. However, the test instrument, such as measuring apparatus 10 must be equipped with force sensors for the orthogonal direction (e.g. Hysitron TriboIndenter system with a Hysitron 3D OmniProbe head).

Figure 7:
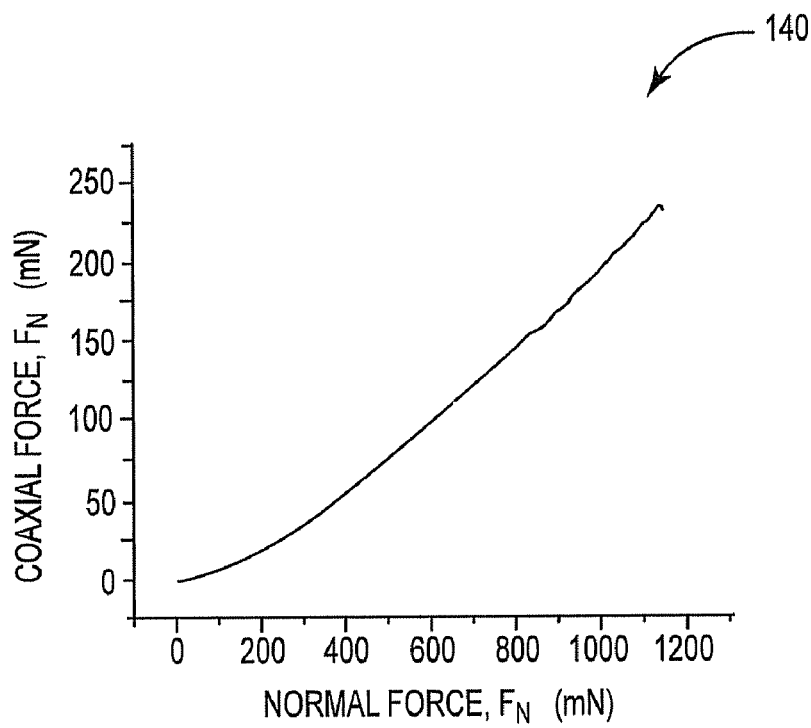
FIG. 7 is a graph of coaxial force versus normal force for a test sample.
Figure 8:
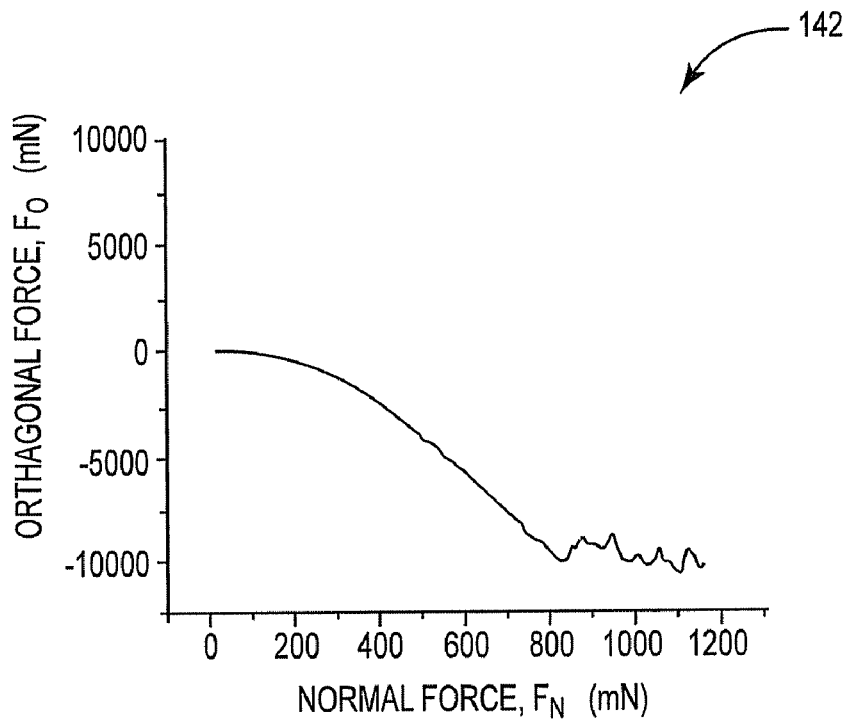
FIG. 8 is a graph of orthogonal force versus normal force for a test sample.

Although described primarily above with respect to scratching a coating applied to a substrate surface, it is noted that the embodiment according to the present disclosure can also be applied to directly test the surface of an uncoated substrate, such as glass, for example. FIGS. 7 and 8 illustrate the operation of measuring apparatus 10, according to the present disclosure, as applied to a glass sample having no coating. In the example of FIGS. 7 and 8, material 18 of sample 16 comprises glass, and surface 20 comprises a surface of the glass sample (i.e. the glass has no thin-film or coating thereon). According to the example of FIGS. 7 and 8, normal force $F_N$ 30 was ramped from 0 to 1.5 N. FIG. 7 is a graph 140 of coaxial force $F_C$ 32 versus normal force $F_N$ 30. With reference to graph 140, by using the conventional technique of detecting deviations in coaxial force $F_C$ 32 to determine a critical load, it can be seen that it is difficult to detect a critical load or normal force $F_N$ 30 at which the coating fractures.

FIG. 8 is a graph 142 of orthogonal force $F_O$ 34 versus normal force $F_N$ 30. From graph 142 it can be seen that orthogonal force $F_O$ 34 increases smoothly with increases in normal force $F_N$ 30 until normal force $F_N$ 30 reaches approximately 830 mN, at which point orthogonal force $F_O$ 34 transitions to a much more variable signal. This critical load of 830 mN coincides with the onset of fracture of the glass sample.

Figure 9:
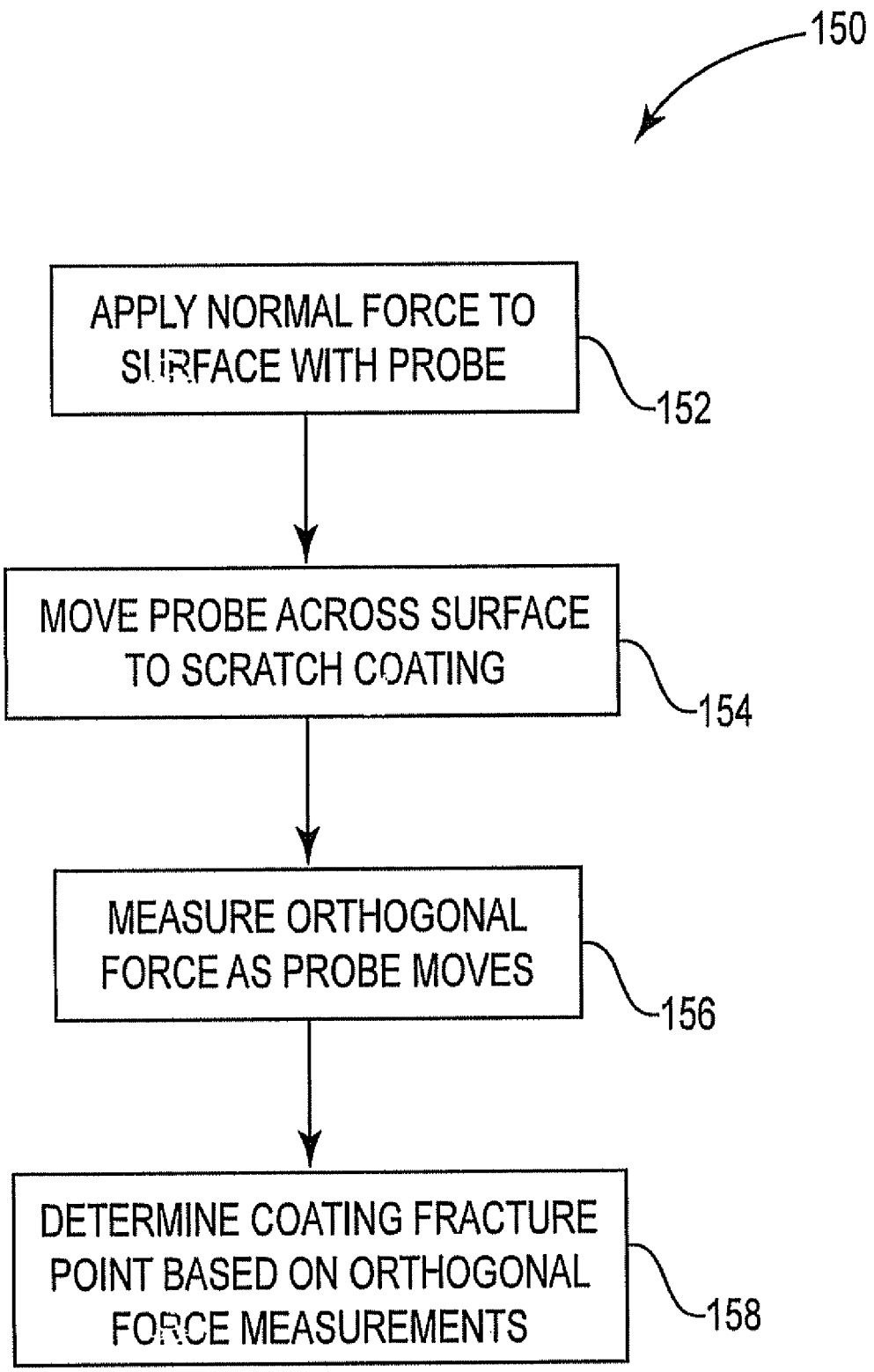
FIG. 9 is a flow diagram illustrating one embodiment of surface testing method.

FIG. 9 is a flow diagram generally illustrating one embodiment of a process 150 employing monitoring of an orthogonal force on a scratch probe used to scratch a surface coating in order to identify a fracture point of the coating according to the present disclosure. Process 150 begins at 152 with the application of a normal force with a scratch probe to a coating joined to a substrate, such as scratch probe 12 applying normal force $F_N$ 30 to coating 20 joined to substrate 18 of device 16 as described above with respect to FIGS. 1 and 2. The term normal force as used herein is defined as force being substantially perpendicular to coating 20.

At 154, the probe is moved linearly across the coating, such as by controller 24 of FIG. 1, to generate a force against and to scratch the coating, the force being substantially parallel to the surface and comprising a coaxial force along the scratch and an orthogonal force perpendicular to the scratch. At 156, process 150 includes measuring a magnitude of the orthogonal force as the probe moves across the coating, such as via force sensor 22 of FIG. 1.

At 158, process 150 includes determining a fracture point of the coating by the probe based on changes in the magnitude of the orthogonal force measured at 156. In one embodiment, with reference to FIG. 1, measuring apparatus 10 includes an analyzer module 38, either as a component of or separate from controller 24, which receives displacement and force signals 28 and 29, with force signal 29 representative of the measured normal ($F_N$), coaxial ($F_C$), and orthogonal ($F_O$)

forces 30, 32, and 34. According to one embodiment, analyzer module 38 is configured to monitor and detect changes or deviations in the magnitude of orthogonal force $F_O$ which are indicative of a fracture of coating 20.

According to one embodiment, analyzer module 38 is configured to calculate an expected value for a next measured orthogonal force value provided by force signal from previously measured orthogonal force values. In one embodiment, if the actual value of the next measured orthogonal force value deviates from the expected value by more than a predetermined amount, it is deemed to be an indication that a fracture of coating 20 has occurred. According to one embodiment, the actual value of a plurality of "next" measured orthogonal force values must deviate from an expected value by the predetermined amount before a fracture of coating 20 is deemed to have occurred (i.e. the orthogonal force must deviate from expected values for a predetermined time period).

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method of evaluating a performance of a surface of a material, the method comprising:
   applying a normal force with a probe to a surface of a material, the normal force being substantially perpendicular to the surface;
   moving the probe across the surface to generate a force against and to scratch the surface, the force being substantially parallel to the surface and comprising a coaxial force along the scratch and an orthogonal force perpendicular to the scratch;
   measuring a magnitude of the orthogonal force as the probe moves across the surface; and
   determining a fracture point of the surface by the probe based on changes in the magnitude of the orthogonal force.

2. The method of claim 1, including:
   rating a performance of the surface based on the magnitude of the normal force at the fracture point of the surface.

3. The method of claim 1, determining a fracture point includes:
   determining expected values for the magnitude of the orthogonal force based previous measurements of the magnitude of the orthogonal force as the probe moves across the surface; and
   deeming a fracture point to have occurred when measured values of the magnitude of the orthogonal force deviate from the expected values.

4. The method of claim 3, wherein deeming a fracture point to have occurred when a predetermined number of successive measured values of the magnitude of the orthogonal force deviate from corresponding expected values by at least the predetermined amount.

5. The method of claim 1, wherein the surface comprises a coating joined to the material.

6. The method of claim 1, wherein applying the normal force includes applying the normal force with a substantially constant magnitude.

7. The method of claim 1, wherein applying the normal force includes applying the normal force with a magnitude which increases as the probe moves across the surface.

8. The method of claim 7, wherein the magnitude of the normal force is ramped in a linear fashion from an unload condition to a predetermined magnitude.

9. A system for evaluating a performance of a surface of a material including:
   a probe;
   a controller configured to apply, with the probe, a normal force to a surface of a material, and to move the probe across the surface to generate a lateral force against and to scratch the surface, the lateral force being substantially parallel to a surface and comprising coaxial force along the scratch and an orthogonal force perpendicular to the scratch;
   a force sensor configured to measure a magnitude of at least the normal force and the orthogonal force; and
   an analyzer module configured to determine a fracture point of the surface based on changes in magnitude of the orthogonal force.

10. The system of claim 9, wherein the analyzer module is configured to determine a magnitude of the normal force at the fracture point of the surface, with said magnitude of the normal force is representative of a performance rating of the surface.

11. The system of claim 9, wherein to determine a fracture point the analyzer module is configured to determine expected values for the magnitude of the orthogonal force as the probe moves across the surface based on previously measured values of the magnitude of the orthogonal force, and to compare the expected values to corresponding measured values after being measured by the force sensor.

12. The system of claim 11, wherein the force analyzer provides an indication of a fracture point when the corresponding measured values of the magnitude deviate from the expected values.

13. The system of claim 12, wherein the force analyzer provides indication of a fracture point when the corresponding measured values of the magnitude deviate from the expected values by at least a predetermined amount for one or more successive expected values.

14. The system of claim 9, wherein the surface comprises a coating joined to the material.

15. The system of claim 9, wherein the controller applies the normal force with a substantially constant magnitude.

16. The method of claim 9, wherein the controller applies the normal force with an increasing magnitude as the probe moves across the surface.

17. A method of detecting failure of a surface of a material comprising:
   applying a normal force to a surface of a material with a tip of a scratch probe;
   moving the scratch probe across the surface to scratch the surface;
   measuring a magnitude of an orthogonal force on the tip as the scratch probe moves across the surface, the orthogonal force being perpendicular to the scratch; and
   identifying a fracture point of the surface based on changes in magnitude of the orthogonal force as the scratch probe moves across the surface.

18. The method of claim 17, wherein the surface comprises a coating joined to the material.

19. The method of claim 17, wherein applying a normal force includes applying the normal force with a constant magnitude.

20. The method of claim 17, wherein applying a normal force includes applying the normal force with an increasing magnitude as the scratch probe moves across the surface coating.

* * * * *